United States Patent
Nakamura et al.

(10) Patent No.: US 9,099,635 B2
(45) Date of Patent: Aug. 4, 2015

(54) ULTRASONIC TRANSDUCER ELEMENT CHIP, PROBE, ELECTRONIC INSTRUMENT, AND ULTRASONIC DIAGNOSTIC DEVICE

(71) Applicant: SEIKO EPSON CORPORATION, Tokyo (JP)

(72) Inventors: Tomoaki Nakamura, Nagano (JP); Jiro Tsuruno, Nagano (JP); Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 352 days.

(21) Appl. No.: 13/770,115

(22) Filed: Feb. 19, 2013

(65) Prior Publication Data

US 2013/0223191 A1 Aug. 29, 2013

(30) Foreign Application Priority Data

Feb. 24, 2012 (JP) ................. 2012-038402

(51) Int. Cl.
*H01L 41/053* (2006.01)
*B06B 1/06* (2006.01)

(52) U.S. Cl.
CPC ............ *H01L 41/053* (2013.01); *B06B 1/0629* (2013.01)

(58) Field of Classification Search
CPC ............................ B06B 1/0629; H01L 41/053
USPC ........................................................ 367/135
See application file for complete search history.

(56) References Cited

U.S. PATENT DOCUMENTS

| 8,169,855 | B2 | 5/2012 | Nakamura | |
|---|---|---|---|---|
| 2011/0074246 | A1 | 3/2011 | Nishie et al. | |
| 2011/0115337 | A1 | 5/2011 | Nakamura et al. | |
| 2012/0188850 | A1 | 7/2012 | Nakamura | |
| 2013/0223191 | A1* | 8/2013 | Nakamura et al. | 367/135 |
| 2013/0258802 | A1* | 10/2013 | Nakamura et al. | 367/7 |
| 2013/0258803 | A1* | 10/2013 | Nakamura et al. | 367/7 |

FOREIGN PATENT DOCUMENTS

| JP | 2010-183437 A | 8/2010 |
|---|---|---|
| JP | 2010-210283 A | 9/2010 |
| JP | 2011-077918 A | 4/2011 |
| JP | 2011-082624 A | 4/2011 |
| JP | 2011-124973 A | 6/2011 |

\* cited by examiner

*Primary Examiner* — Daniel Pihulic
(74) *Attorney, Agent, or Firm* — Global IP Counselors, LLP

(57) ABSTRACT

An ultrasonic transducer element chip includes a substrate, a plurality of ultrasonic transducer elements and a plate-shaped member. The substrate includes a partition wall section defining a plurality of openings arranged in an array pattern. A wall thickness of the partition wall section is smaller than a wall height of partition wall section. Each of the ultrasonic transducer elements is provided in each of the openings. The plate-shaped member is fixed on a surface of the substrate opposite to a surface of the substrate on which the ultrasonic transducer elements are provided. The plate-shaped member covers at least one of the openings in a plan view seen along a thickness direction of the substrate.

13 Claims, 7 Drawing Sheets

ULTRASONIC TRANSDUCER ELEMENT CHIP, PROBE, ELECTRONIC INSTRUMENT, AND ULTRASONIC DIAGNOSTIC DEVICE

CROSS-REFERENCE TO RELATED APPLICATIONS

This application claims priority to Japanese Patent Application No. 2012-038402 filed on Feb. 24, 2012. The entire disclosure of Japanese Patent Application No. 2012-038402 is hereby incorporated herein by reference.

BACKGROUND

1. Technical Field

The present invention relates to an ultrasonic transducer element chip, a probe that uses the ultrasonic transducer element chip, and an electronic instrument and an ultrasonic diagnostic device that use the probe.

2. Related Art

As described in Japanese Laid-Open Patent Publication No. 2011-82624, for example, an ultrasonic transducer element chip is provided with a substrate. A plurality of openings are formed in the substrate. An ultrasonic transducer element is provided in each of the openings. The ultrasonic transducer element chip is provided with a vibrating film. The vibrating film covers the openings from a surface of the substrate.

SUMMARY

When the openings are formed in the substrate, the strength of the substrate is deteriorated. The strength is insufficient with respect to force in a thickness direction of the substrate. Therefore, when the ultrasonic transducer element chip is pressed against a target to be tested, the ultrasonic transducer element chip will often be damaged.

According to at least one embodiment of the present invention, an ultrasonic transducer element chip that is thin and has sufficient strength in a thickness direction of a substrate can be provided.

An ultrasonic transducer element chip according to one aspect of the present invention includes a substrate, a plurality of ultrasonic transducer elements and a plate-shaped member. The substrate includes a partition wall section defining a plurality of openings arranged in an array pattern. A wall thickness of the partition wall section is smaller than a wall height of partition wall section. Each of the ultrasonic transducer elements is provided in each of the openings. The plate-shaped member is fixed on a surface of the substrate opposite to a surface of the substrate on which the ultrasonic transducer elements are provided. The plate-shaped member covers at least one of the openings in a plan view seen along a thickness direction of the substrate.

In this ultrasonic transducer element chip, the ultrasonic transducer element can be formed to be thin. The ultrasonic transducer element can be formed in a thin substrate. Even in a case where the plate-shaped member is fixed to a substrate, the ultrasonic transducer element chip can be formed to be thin. At the same time, the plate-shaped member reinforces the strength of the substrate. In particular, since the wall thickness of the partition wall section between the openings is smaller than the wall height of the partition wall section between the openings, the sufficient rigidity of the partition wall section can be obtained in the thickness direction of the substrate due to the section modulus. Force in the thickness direction of the substrate is transmitted through the partition wall section and supported by the plate-shaped member. In this manner, the ultrasonic transducer element chip has sufficient strength in the thickness direction of the substrate. Here, the partition wall section corresponds to parts of the substrate sandwiched between spaces of the adjacent openings. The wall thickness refers to the thickness of the partition wall section, that is, the distance between the openings. When the wall surface of the partition wall section is a flat surface, the wall thickness can be defined as the length of the perpendicular line that is orthogonal to the wall surface. The wall height can be defined as the length of the wall surface defined in the thickness direction of the substrate.

In the ultrasonic transducer element chip, the plate-shaped member is preferably bonded to at least one bonding region of the partition wall section. When the partition wall section is bonded to the plate-shaped member, the movement of the partition wall section is restricted by the plate-shaped member. Thus, vibration of the partition wall section can be prevented. As a result, cross talk between the ultrasonic transducer elements can be prevented. Further, when the movement of the partition wall section is restricted, vibration of the partition wall section can be prevented from acting on ultrasonic vibration of the ultrasonic transducer elements. Then, ultrasonic vibration in a clear vibration mode can be obtained in the ultrasonic transducer elements. Consequently, when vibration of the partition wall section is avoided, the amplitude of ultrasonic vibration can be prevented from being decreased.

In the ultrasonic transducer element chip, the partition wall section is preferably arranged so that an outline of each the openings is defined as a quadrangle. When the openings having a quadrangular outline are adjacent to each other, the partition wall section has a uniform wall thickness. In particular, as the density of the ultrasonic transducer elements increases, the wall thickness of the partition wall section uniformly decreases. Therefore, the rigidity of the partition wall section is significantly deteriorated. In such an instance, by bonding the partition wall section to the plate-shaped member, vibration of the partition wall section can be effectively prevented.

In the ultrasonic transducer element chip, the quadrangle preferably has two opposed long sides, and the bonding region of the partition wall section is preferably a region including a center position of each of the long sides. Therefore, a part of the partition wall section in which the amplitude of vibration is large is bonded to the plate-shaped member. As a result, vibration of the partition wall section can be effectively prevented.

In the ultrasonic transducer element chip, the bonding region of the partition wall section is preferably a region including an entire length of each of the long sides. When the partition wall section is bonded to the plate-shaped member over the entire length of the long side, vibration of the partition wall section can be securely prevented.

In the ultrasonic transducer element chip, the partition wall section is preferably surface-bonded to the plate-shaped member over an entire surface corresponding to each of the long sides disposed between the openings. When the partition wall section is surface-bonded to the plate-shaped member with respect to the entire surface between the openings over the entire length of the long side, vibration of the partition wall section can be securely prevented.

In the ultrasonic transducer element chip, the partition wall section corresponding to each side of the quadrangle preferably includes the bonding region. When the partition wall section is bonded to the plate-shaped member in each side of the quadrangle, vibration of the partition wall section can be securely prevented.

In the ultrasonic transducer element chip, the bonding region of the partition wall section preferably continuously surrounds the quadrangle. When the partition wall section is bonded to the plate-shaped member with respect to the entire region of the quadrangle, vibration of the partition wall section can be securely prevented.

In the ultrasonic transducer element chip, the partition wall section is preferably surface-bonded to the plate-shaped member over an entire surface corresponding to an entire periphery of the quadrangle. When the partition wall section is surface-bonded to the plate-shaped member with respect to the entire surface between the openings over the entire periphery of the quadrangle, vibration of the partition wall section can be securely prevented.

A probe according to another aspect of the present invention includes the ultrasonic transducer element chip as described above, and a case member supporting the ultrasonic transducer element chip.

An electronic instrument according to another aspect of the present invention includes the probe as described above, and a processing circuit connected to the probe and configured to process an output signal from the ultrasonic transducer element.

An ultrasonic diagnostic according to another aspect of the present invention includes the probe as described above, a processing circuit connected to the probe and configured to process an output signal from the ultrasonic transducer element to generate an image, and a display device configured to display the image.

A probe head according to another aspect of the present invention includes the ultrasonic transducer element chip as described above, and a case member supporting the ultrasonic transducer element chip, and configured to be coupled to a probe main body.

BRIEF DESCRIPTION OF THE DRAWINGS

Referring now to the attached drawings which form a part of this original disclosure.

DETAILED DESCRIPTION OF EXEMPLARY EMBODIMENTS

Next, embodiments of the present invention will be explained with reference to the attached drawings. The embodiments explained below shall not be construed as unreasonably limiting the subject matter of the present invention described in the claims, and all the elements explained in the embodiments are not necessarily essential to the solving means of the present invention.

(1) Overall Configuration of Ultrasonic Diagnostic Device

Figure 1:
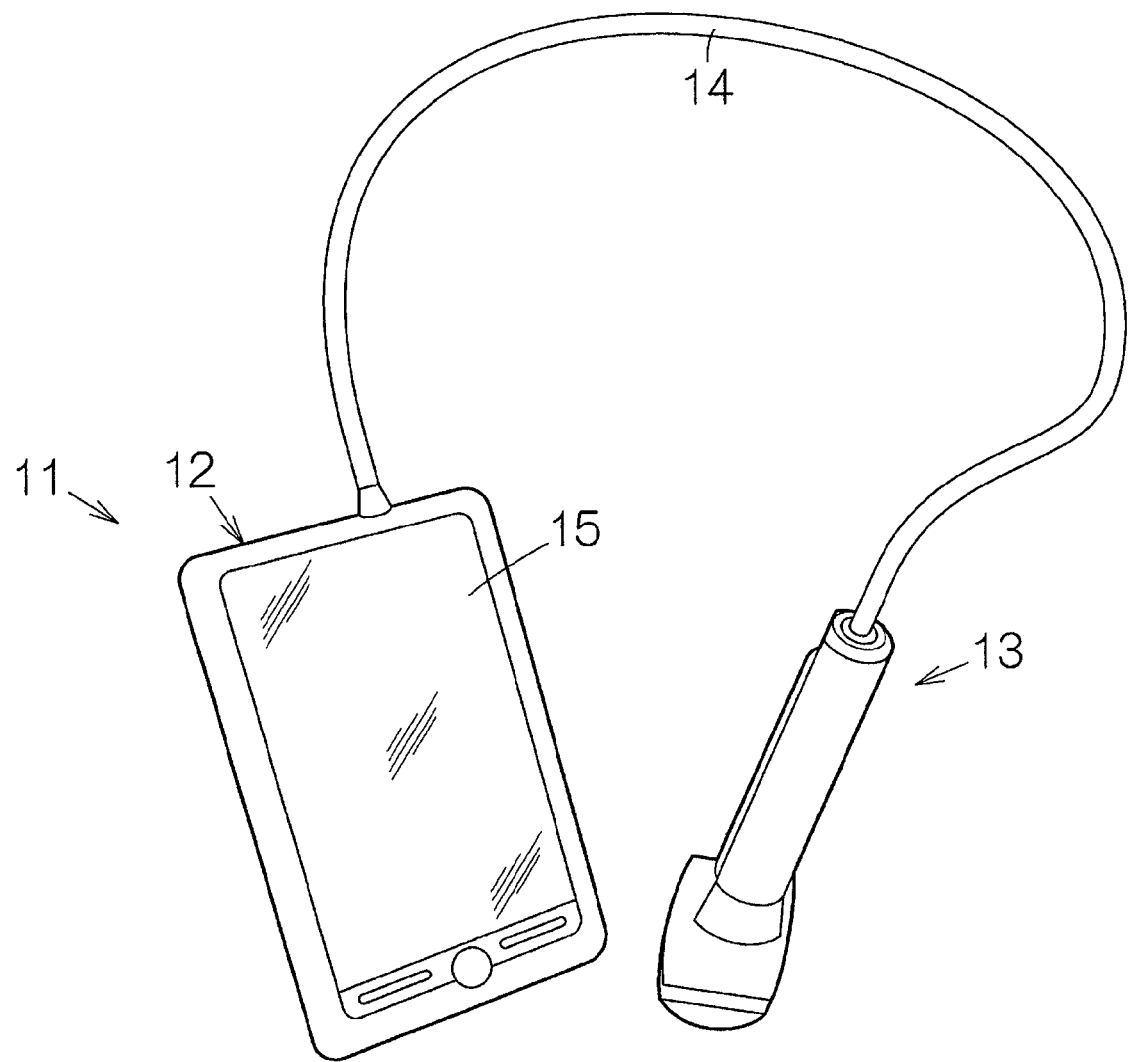
FIG. 1 is a perspective view schematically showing an example of an electronic instrument, that is, an ultrasonic diagnostic device according to one embodiment of the present invention.

FIG. 1 schematically shows a configuration of an ultrasonic diagnostic device 11 as an example of an electronic instrument according to an embodiment of the present invention. The ultrasonic diagnostic device 11 is provided with a device terminal 12 and an ultrasonic probe 13 (one example of a probe). The device terminal 12 and the ultrasonic probe 13 are connected to each other through a cable 14. The device terminal 12 and the ultrasonic probe 13 communicate an electric signal through the cable 14. A display panel 15 (one example of a display device) is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
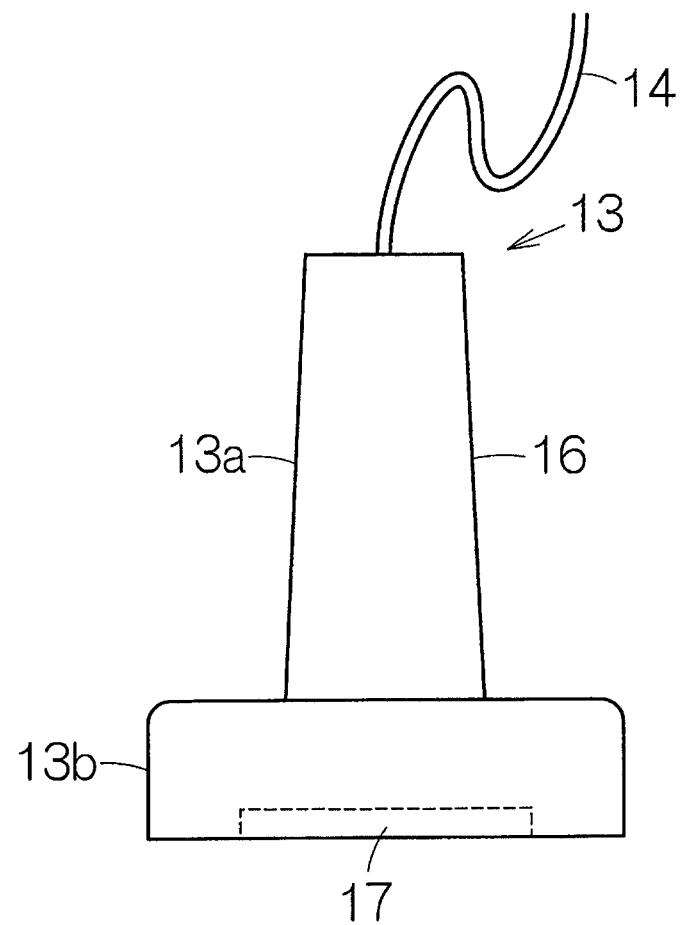
FIG. 2 is an enlarged front view of an ultrasonic probe.

As shown in FIG. 2, the ultrasonic probe 13 has a case 16 (one example of a case member). An ultrasonic transducer element chip (hereinafter referred to as "element chip") 17 is accommodated in the case 16. A surface of the element chip 17 may be exposed on a surface of the case 16. The element chip 17 outputs ultrasonic waves from the surface thereof, and receives reflected waves of ultrasonic waves. Also, the ultrasonic probe 13 may be provided with a probe head 13b removably coupled with a probe main body 13a. In such an instance, the element chip 17 may be incorporated in the case 16 of the probe head 13b, and the case 16 of the probe head 13b is configured to be coupled to the probe main body 13a.

(2) Configuration of Ultrasonic Transducer Element Chip

Figure 3:
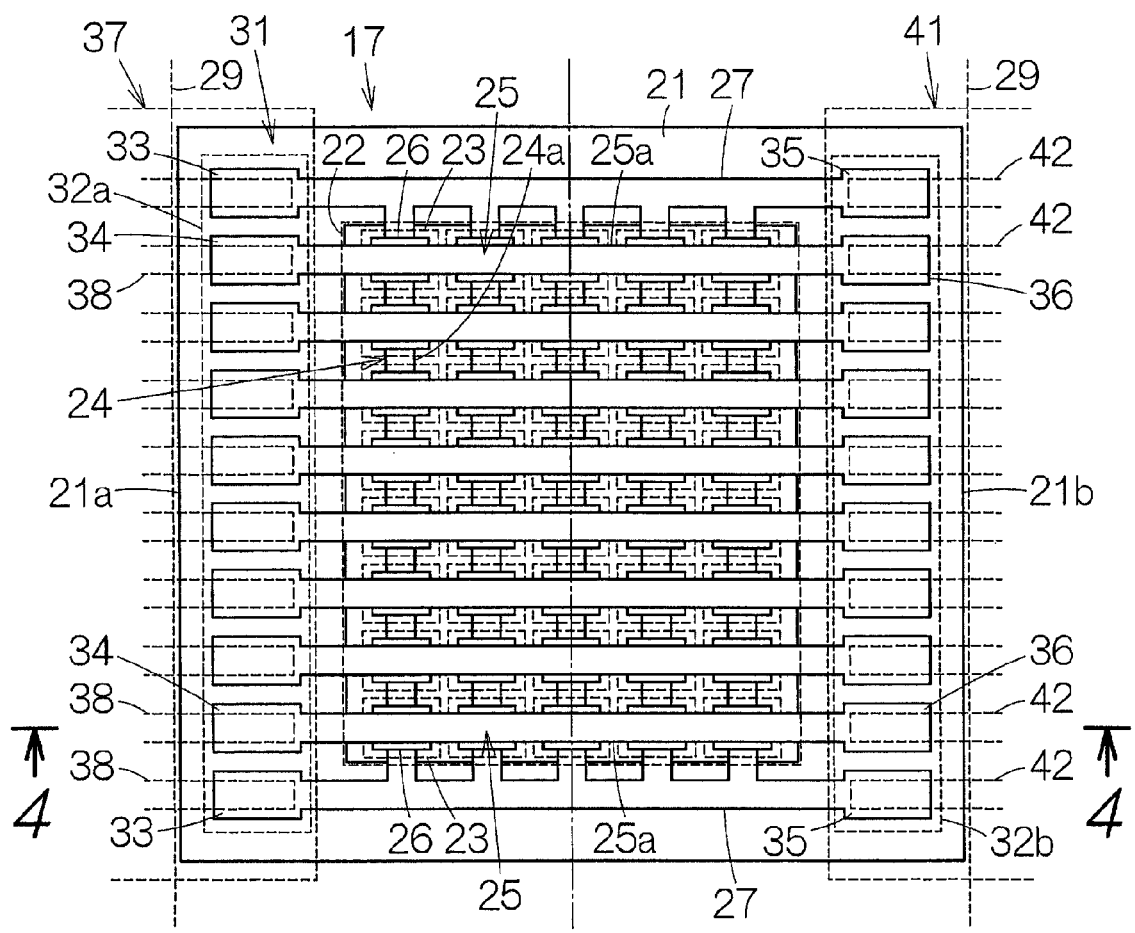
FIG. 3 is an enlarged plan view of an ultrasonic transducer element chip.

FIG. 3 schematically shows a plan view of the element chip 17 according to an embodiment of the present invention. The element chip 17 is provided with a substrate 21. An element array 22 is formed on a surface of the substrate 21. The element array 22 is constructed with an arrangement of an ultrasonic transducer element (hereinafter referred to as "element") 23. The arrangement is formed in a matrix having a plurality of columns and a plurality of rows. Each element 23 has a piezoelectric element section. The piezoelectric element section is constructed of a lower electrode 24, an upper electrode 25, and a piezoelectric film 26. The piezoelectric film 26 is sandwiched between the lower electrode 24 and the upper electrode 25 in each element 23.

The lower electrode 24 has a plurality of first conductive bodies 24a. The first conductive bodies 24a extend in a row direction of the arrangement in parallel to each other. One first conductive body 24a is assigned to each row of the elements 23. One first conductive body 24a is provided in common with respect to the piezoelectric films 26 of the elements 23 lined up in the row direction of the arrangement. Both ends of the first conductive body 24a are connected to a pair of extraction wirings 27, respectively. The extraction wirings 27 extend in a column direction of the arrangement in parallel to each other. All the first conductive bodies 24a have the same length. In this manner, the lower electrode 24 is provided in common with respect to the elements 23 of the entire matrix.

The upper electrode 25 has a plurality of second conductive bodies 25a. The second conductive bodies 25a extend in a column direction of the arrangement in parallel to each other. One second conductive body 25a is assigned to each column of the elements 23. One second conductive body 25a is provided in common with respect to the piezoelectric films 26 of the elements 23 lined up in the column direction of the arrangement. Power distribution to the elements 23 is switched per column. Line scanning or sector scanning is achieved corresponding to such switching of power distribution. Since the elements 23 in one column output ultrasonic waves at the same time, the number of the elements 23 in one column, that is, the row number of the arrangement can be determined based on the output level of ultrasonic waves. For example, the row number may be set to be around 10-15. In the drawing, five rows are illustrated for simplicity. The column number of the arrangement can be determined based on the extent of an area to be scanned. For example, the column number may be set to be 128 or 256. In the drawing, eight columns are illustrated for simplicity. Regarding the arrangement, a zigzag pattern may be used. In the zigzag pattern, a group of the elements 23 in an even column may be displaced with respect to a group of the elements 23 in an odd column by one-half of the row pitch. The number of the elements in one of an odd column and an even column may be smaller than the number of the elements in the other of an odd column and an even column by one. Further, the role of the lower electrode 24 and the role of the upper electrode 25 may be switched. Specifically, the upper electrode may be connected in common to the elements 23 of the entire matrix, and the lower electrode may be connected in common to the elements 23 in each column of the arrangement.

The outer edge of the substrate 21 has a first side 21a and a second side 21b that are opposed and partitioned by a pair of straight lines 29 parallel to each other. A peripheral region 31 extends between the outline of the element array 22 and the outer edge of the substrate 21. In the peripheral region 31, a first terminal array 32a of one line is arranged between the first side 21a and the outline of the element array 22, and a second terminal array 32b of one line is arranged between the second side 21b and the outline of the element array 22. The line of the first terminal array 32a can be made parallel to the first side 21a. The line of the second terminal array 32b can be made parallel to the second side 21b. The first terminal array 32a is constructed of a pair of lower electrode terminals 33 and a plurality of upper electrode terminals 34. Similarly, the second terminal array 32b is constructed of a pair of lower electrode terminals 35 and a plurality of upper electrode terminals 36. The lower electrode terminal 33 and the lower electrode terminal 35 are connected to both ends of each of the extraction wiring 27, respectively. It is sufficient for the extraction wirings 27, the lower electrode terminals 33 and the lower electrode terminals 35 to be formed plane-symmetrically with respect to a vertical plane that bisects the element array 22. The upper electrode terminal 34 and the upper electrode terminal 36 are connected to both ends of each of the second conductive bodies 25a, respectively. It is sufficient for the second conductive bodies 25a, the upper electrode terminals 34 and the upper electrode terminals 36 to be formed plane-symmetrically with respect to the vertical plane that bisects the element array 22.

A first flexible printed substrate 37 is coupled with the substrate 21. The first flexible printed substrate 37 covers the first terminal array 32a. Conductive line, that is, first signal lines 38 are formed at one end of the first flexible printed substrate 37 corresponding to the lower electrode terminals 33 and the upper electrode terminals 34, respectively. The first signal lines 38 are respectively opposed to the lower electrode terminals 33 and the upper electrode terminals 34, and respectively bonded thereto. Similarly, a second flexible printed substrate 41 is coupled with the substrate 21. The second flexible printed substrate 41 covers the second terminal array 32b. Conductive lines, that is, second signal lines 42 are formed at a first end 41a of the second flexible printed substrate 41 corresponding to the lower electrode terminals 35 and the upper electrode terminals 36, respectively. The second signal lines 42 are respectively opposed to the lower electrode terminals 35 and the upper electrode terminals 36, and respectively bonded thereto.

Figure 4:
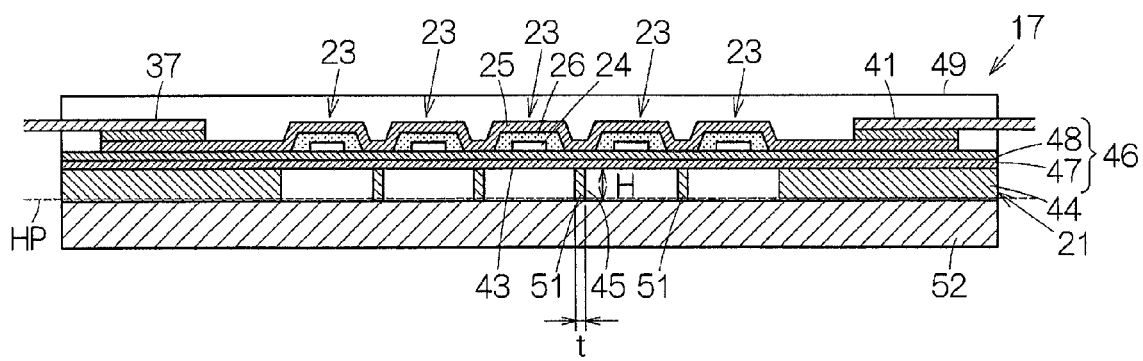
FIG. 4 is a sectional view along line 4-4 of FIG. 3.

As shown in FIG. 4, each of the elements 23 has a vibrating film 43. In order to achieve the vibrating film 43, an opening 45 is formed in each of the elements 23 on a substrate base 44 of the substrate 21. The openings 45 are arranged in an array pattern with respect to the substrate base 44. A flexible film 46 is formed all over a surface of the substrate base 44. The flexible film 46 is constructed of a silicon oxide ($SiO_2$) layer 47 layered on the surface of the substrate base 44, and a zirconium oxide ($ZrO_2$) layer 48 layered on a surface of the silicon oxide layer 47. The flexible film 46 contacts the openings 45. In this manner, a part of the flexible film 46 serves as the vibrating film 43 corresponding to the outline of the opening 45. The film thickness of the silicon oxide layer 47 can be determined based on the resonance frequency.

The lower electrode 24, the piezoelectric film 26, and the upper electrode 25 are layered on a surface of the vibrating film 43 in this order. As for the lower electrode 24, a layered film of titanium (Ti), iridium (Ir), platinum (Pt), and titanium (Ti) can be used, for example. The piezoelectric film 26 may be formed of piezoelectric zirconate titanate (PZT), for example. The upper electrode 25 may be formed of iridium (Ir), for example. Another conductive material may be used for the lower electrode 24 and the upper electrode 25. Another piezoelectric material may be used for the piezoelectric film 26. The piezoelectric film 26 completely covers the lower electrode 24 under the upper electrode 25. The function of the piezoelectric film 26 prevents short circuit between the upper electrode 25 and the lower electrode 24 from occurring.

A protective film 49 is layered on the surface of the substrate 21. The protective film 49 covers, for example, the entire surface of the substrate 21. As a result, the protective film 49 covers the element array 22, the first terminal array 32a, the second terminal array 32b, a first end 37a of the first flexible printed substrate 37, and the first end 41a of the second flexible printed substrate 41. For example, a silicone resin film may be used for the protective film 49. The protective film 49 protects the configuration of the element array 22, the bonding of the first terminal array 32a and the first flexible printed substrate 37, and the bonding of the second terminal array 32b and the second flexible printed substrate 41.

A partition wall 51 (one example of a partition wall section) is laid out between the openings 45 adjacent in the row direction and the column direction of the matrix. The openings 45 are partitioned by the partition wall 51. The wall thickness "t" of the partition wall 51 corresponds to the distance between the hollow spaces of the openings 45. The partition wall 51 has two wall surfaces in planes extending in parallel to each other. The wall thickness "t" of the partition wall 51 corresponds to the distance between the wall surfaces. Specifically, the wall thickness "t" of the partition wall 51 corresponds to the length of a perpendicular line that is orthogonal to the wall surfaces and is sandwiched by the wall surfaces. When the wall thickness of the partition wall 51 varies along the thickness direction of the substrate 21 (for example, see FIG. 10), the wall thickness "t" refers to a maximum length between the wall surfaces of the partition wall 51. The wall height "H" of the partition wall 51 corresponds to the depth of the opening 45. The depth of the opening 45 corresponds to the thickness of the substrate base 44. Therefore, the wall height "H" of the partition wall 51 can be defined as the length of the wall surface defined in the thickness direction of the substrate base 44. Since the substrate base 44 has a uniform thickness, the partition wall 51 can have a uniform wall height "H" over the entire length. When the wall thickness "t" of the partition wall 51 is decreased, the arrangement density of the vibrating film 43 can be increased. This can contribute to downsizing of the element chip 17. When the wall height "H" of the partition wall 51 is larger than the wall thickness "t" of the partition wall 51, the bending rigidity of the element chip 17 can be increased. Consequently, the distance between the openings 45 is set to be smaller than the depth of the opening 45.

A reinforcing plate 52 (one example of a plate-shaped member) is fixed to a rear surface of the substrate base 44. The rear surface of the substrate base 44 is layered on a surface of the reinforcing plate 52. The surface of the reinforcing plate 52 extends in a hypothetical plane HP. Since the rear surface of the substrate base 44 also extends in the hypothetical plane HP, the rear surface of the substrate base 44 can contact the surface of the reinforcing plate 52 with an area as large as possible. The reinforcing plate 52 closes the openings 45 in a rear surface of the element chip 17. The reinforcing plate 52 covers the openings 45 in a plan view along a thickness direction of the substrate base 44. The reinforcing plate 52 may have a rigid base material. For example, the reinforcing plate 52 may be formed of a silicon base plate. The plate thickness of the substrate base 44 is set to be around 100 µm, and the plate thickness of the reinforcing plate 52 is set to be around 100-150 µm. The partition walls 51 are bonded to the reinforcing plate 52. The reinforcing plate 52 is bonded to each of the partition walls 51 in at least one bonding region. An adhesive can be used for bonding.

Figure 5:
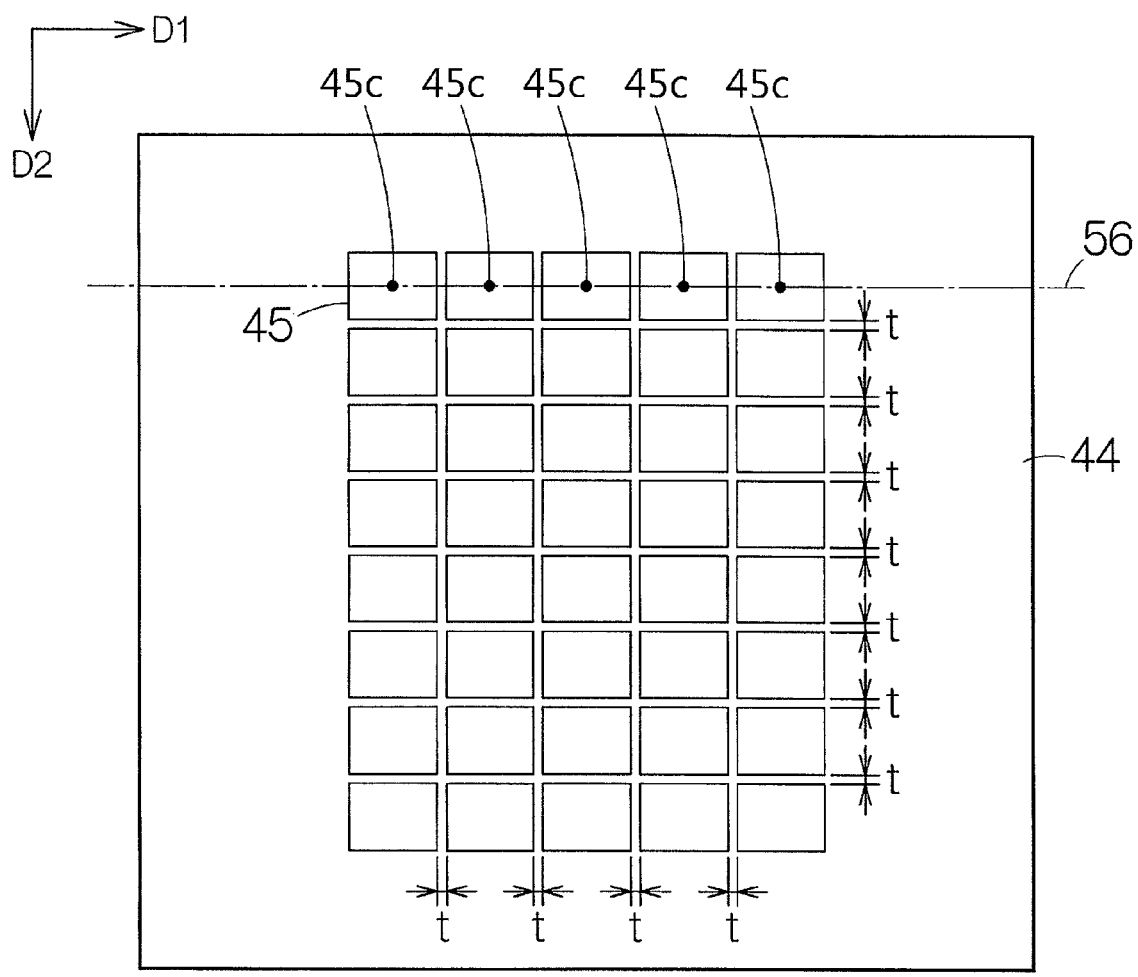
FIG. 5 is a plan view of a rear surface of a substrate base.

As shown in FIG. 5, the openings 45 form a line in a first direction D1. The centroids 45c of the outlines of the openings 45 are located on a straight line 56 in the first direction D1 at equal pitches. Since the openings 45 are formed by copying a single outline shape, the openings 45 of the same shape are repeatedly arranged at uniform pitches. For example, an outline 45a of the opening 45 is defined as a quadrangle. Specifically, the outline 45a of the opening 45 is formed in a rectangle. The long side of the rectangle is made to coincide with the first direction D1. Since the opening 45 has the rectangular outline 45a, the partition wall 51 can have a uniform wall thickness "t" over the entire length. In such an instance, the bonding region of the partition walls 51 may be a region that includes a center position of the long side. In particular, the bonding region of the partition walls 51 may be a region that includes the entire length of the long side. The partition walls 51 may be surface-bonded to the reinforcing plate 52 with respect to the entire surface between the openings 45 over the entire length of the long side. The bonding region of the partition walls 51 may be located in at least one position of each side of the quadrangle. The bonding region of the partition walls 51 may continuously surround the quadrangle. The partition walls 51 may be surface-bonded to the reinforcing plate 52 with respect to the entire surface between the openings 45 over the entire periphery of the quadrangle.

(3) Circuit Configuration of Ultrasonic Diagnostic Device

Figure 6:
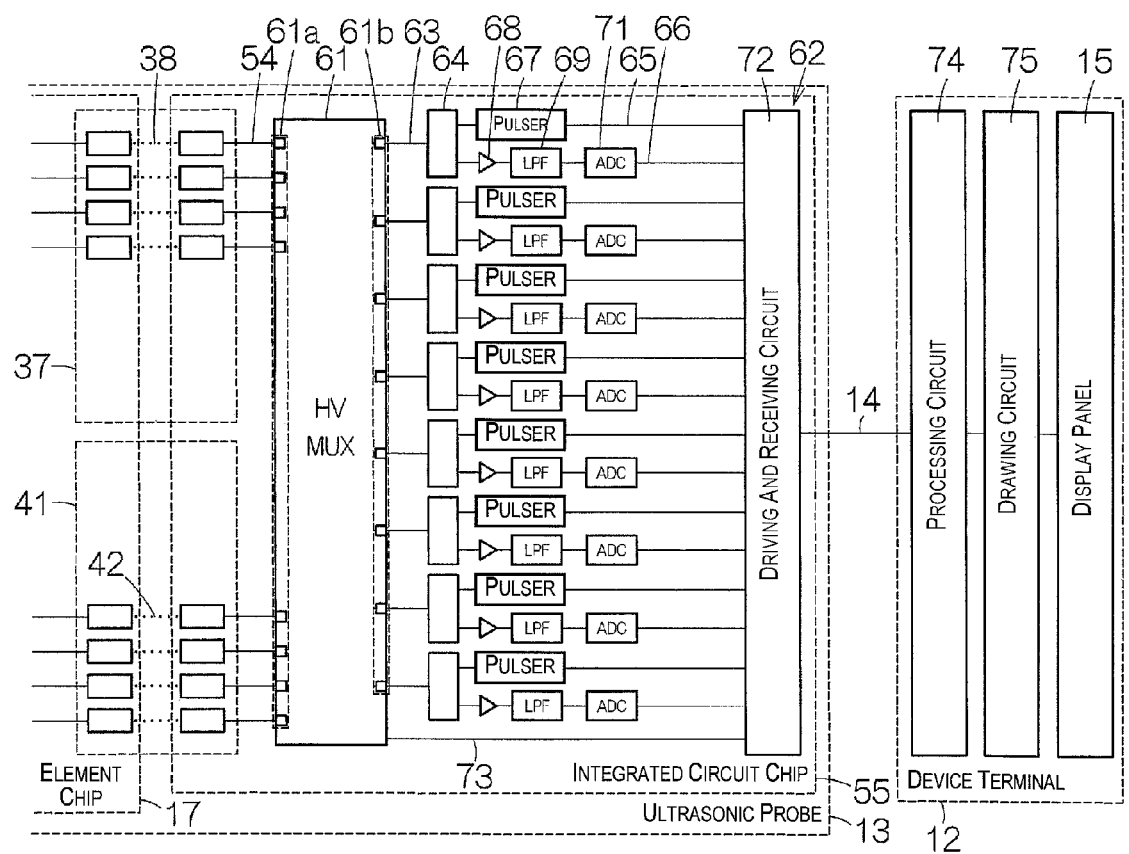
FIG. 6 is a block diagram schematically showing a circuit configuration of the ultrasonic diagnostic device.

As shown in FIG. 6, an integrated circuit has a multiplexer 61, and a transmitting and receiving circuit 62. The multiplexer 61 has a group of ports 61a on the element chip 17 side, and a group of ports 61b on the transmitting and receiving circuit 62 side. The first signal lines 38 and the second signal lines 42 are connected to the group of ports 61a via first wirings 54. In this manner, the group of ports 61a are connected to the element array 22. Signal lines 63 are connected to the group of ports 61b on the transmitting and receiving circuit 62 side, and the number of the signal lines 63 is a prescribed number in an integrated circuit chip 55. The prescribed number corresponds to a column number of the elements 23 output at the same time as scanning is conducted. The multiplexer 61 controls interconnection between the ports on the cable 14 side and the ports on the element chip 17 side.

The transmitting and receiving circuit 62 has changing switches 64 of a prescribed number. The changing switches 64 are connected to the corresponding signal lines 63, respectively. The transmitting and receiving circuit 62 has a transmission channel 65 and a reception channel 66 for each of the changing switches 64. The transmission channel 65 and the reception channel 66 are connected to the changing switch 64 in parallel. The changing switch 64 selectively connects the transmission channel 65 and the reception channel 66 to the multiplexer 61. A pulser 67 is incorporated in the transmission channel 65. The pulser 67 outputs a pulse signal at a frequency corresponding to the resonance frequency of the vibrating film 43. An amplifier 68, a low-pass filter (LPF) 69, and an analog-digital converter (ADC) 71 are incorporated in the reception channel 66. A detection signal of each of the elements 23 is amplified, and converted into a digital signal.

The transmitting and receiving circuit 62 has a driving/receiving circuit 72. The transmission channel 65 and the reception channel 66 are connected to the driving/receiving circuit 72. The driving/receiving circuit 72 controls the pulser 67 simultaneously depending on the state of scanning. The driving/receiving circuit 72 receives a digital signal of a detection signal depending on the state of scanning. The driving/receiving circuit 72 is connected to the multiplexer 61 through a control line 73. The multiplexer 61 conducts control of interconnection based on a control signal supplied from the driving/receiving circuit 72.

A processing circuit 74 is incorporated in the device terminal 12. The processing circuit 74 can be provided with a central processing unit (CPU) and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with a detection signal of the element 23. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in accordance with drawing data generated in the processing circuit 74. The driving signal is sent to the display panel 15. As a result, an image is displayed on the display panel 15.

(4) Operation of Ultrasonic Diagnostic Device

Next, the operation of the ultrasonic diagnostic device 11 will be explained briefly. The processing circuit 74 gives the driving/receiving circuit 72 instructions to transmit and receive ultrasonic waves. The driving/receiving circuit 72 supplies a control signal to the multiplexer 61, and supplies a driving signal to each of the pulsers 67. The pulser 67 outputs a pulse signal in response to the supply of the driving signal. The multiplexer 61 connects the port of the group of ports 61a to the port of the group of ports 61b in response to the instructions of the control signal. The pulse signal is supplied to the elements 23 per column through the lower electrode terminals 33, 35 and the upper electrode terminals 34, 36 in response to the selection of the port. The vibrating film 43 vibrates in response to the supply of the pulse signal. As a result, desired ultrasonic waves are emitted toward a target (for example, the inside of a human body).

After ultrasonic waves are transmitted, the changing switch 64 is switched. The multiplexer 61 maintains the connection relation of the ports. The changing switch 64 establishes a connection between the reception channel 66 and the signal line 63 instead of a connection between the transmission channel 65 and the signal line 63. Reflected waves of ultrasonic waves vibrate the vibrating film 43. As a result, a detection signal is output from the element 23. The detection signal is converted into a digital signal, and sent into the driving/receiving circuit 72.

Transmission and reception of ultrasonic waves are repeated. For repeating transmission and reception of ultrasonic waves, the multiplexer 61 changes the connection relation of the ports. As a result, line scanning or sector scanning is achieved. When scanning is finished, the processing circuit 74 generates an image based on the digital signal of the detection signal. The generated image is displayed on the screen of the display panel 15.

In the element chip 17, the element 23 can be formed to be thin. The element 23 can be formed on the thin substrate 21. Even in a case where the reinforcing plate 52 is fixed to the substrate 21, the element chip 17 can be formed to be thin. At the same time, the reinforcing plate 52 reinforces the strength of the substrate 21. In particular, since the wall thickness "t" is smaller than the wall height "H" in the partition wall 51, the sufficient rigidity of the partition wall 51 can be obtained in the thickness direction of the substrate 21 due to the section modulus. Force in the thickness direction of the substrate 21 is transmitted through the partition wall 51 and supported by the reinforcing plate 52. In this manner, the element chip 17 has sufficient strength in the thickness direction of the substrate 21. Accordingly, even when the plate thickness of the substrate 21 is set to be around 100 μm, for example, the reinforcing plate 52 can prevent the substrate 21 from being damaged. On the other hand, in a case where the element array is constructed of a bulk-type ultrasonic transducer element, the plate thickness of the substrate is set to be around several millimeters. Even when the reinforcing plate 52 is bonded, the thickness of the element chip 17 according to the present embodiment can be reduced securely compared to the case where the element array is constructed of a bulk-type ultrasonic transducer element. In addition, since the acoustic impedance of the vibrating film 43 is close to that of a human body compared to a bulk-type ultrasonic transducer element, an acoustic impedance matching layer can be omitted in the element chip 17 unlike in the case of a bulk-type ultrasonic transducer element. Omission of the matching layer can further contribute to making the element chip 17 thinner.

The reinforcing plate 52 is bonded to each of the partition walls 51 in at least one bonding region. When the partition walls 51 are bonded to the reinforcing plate 52, the movement of the partition walls 51 is restricted by the reinforcing plate 52. Thus, vibration of the partition walls 51 can be prevented. As a result, cross talk between the elements 23 can be prevented. Further, when the movement of the partition walls 51 is restricted, vibration of the partition walls 51 can be prevented from acting on ultrasonic vibration of the elements 23.

Then, ultrasonic vibration in a clear vibration mode can be obtained in the elements 23. When vibration of the partition walls 51 is avoided, the amplitude of ultrasonic vibration can be prevented from being decreased. On the other hand, when the partition wall 51 moves, a distorted vibration mode having a lower frequency than the vertical vibration mode of the vibrating film 43 occurs. Furthermore, the kinetic energy of the vibrating film 43 decreases by the movement of the partition wall 51, and the amplitude of the vibration decreases.

When the openings 45 having a quadrangular outline are adjacent to each other, the partition walls 51 can be formed to have a uniform wall thickness "t". Thus, the density of the elements 23 can be increased. As the density of the elements 23 increases, the wall thickness "t" of the partition walls 51 uniformly decreases. Therefore, the rigidity of the partition walls 51 is significantly deteriorated. In such an instance, by bonding the partition walls 51 to the reinforcing plate 52, vibration of the partition walls 51 can be effectively prevented.

The bonding region of the partition walls 51 can be a region that includes a center position of the long side. Therefore, a part of the partition walls 51 in which the amplitude of vibration is large is bonded to the reinforcing plate 52. As a result, vibration of the partition walls 51 can be effectively prevented. Also, the bonding region of the partition walls 51 can be a region that includes the entire length of the long side. When the partition walls 51 are bonded to the reinforcing plate 52 over the entire length of the long side, vibration of the partition walls 51 can be securely prevented. Further, the partition walls 51 can be surface-bonded with respect to the entire surface between the openings 45 over the entire length of the long side. When the partition walls 51 are surface-bonded to the reinforcing plate 52 with respect to the entire surface between the openings 45 over the entire length of the long side, vibration of the partition walls 51 can be securely prevented.

It is sufficient that the bonding region of the partition walls 51 is located in at least one position of each side of the quadrangle. When the partition walls 51 are bonded to the reinforcing plate 52 in each side of the quadrangle, vibration of the partition walls 51 can be securely prevented. Also, the bonding region of the partition walls 51 can continuously surround the quadrangle. When the partition walls 51 are bonded to the reinforcing plate 52 with respect to the entire region of the quadrangle, vibration of the partition walls 51 can be securely prevented. Further, the partition walls 51 can be surface-bonded with respect to the entire surface between the openings 45 over the entire periphery of the quadrangle. When the partition walls 51 are surface-bonded to the reinforcing plate 52 with respect to the entire surface between the openings 45 over the entire periphery of the quadrangle, vibration of the partition walls 51 can be securely prevented.

(5) Method for Manufacturing Ultrasonic Transducer Element Chip

Figure 7:
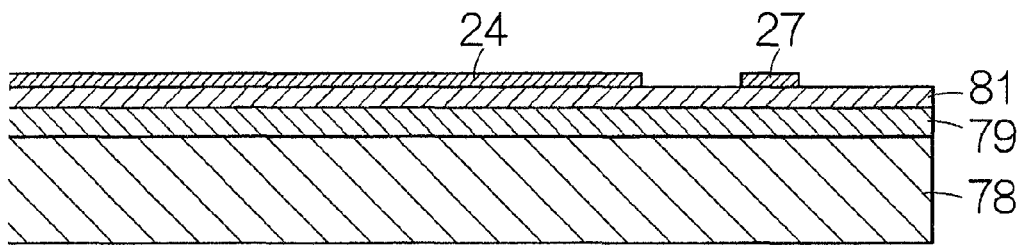
FIG. 7 is a partially enlarged vertical sectional view schematically showing a flexible film and a lower electrode formed on a silicon wafer.

As shown in FIG. 7, the lower electrode 24, the extraction wiring 27, and the lower electrode terminals 33, 35 (not shown in the drawings subsequent to FIG. 7) are formed on a surface of a silicon wafer 78 per each element chip 17. Prior to forming the lower electrode 24, the extraction wiring 27, and the lower electrode terminals 33, 35, a silicon oxide film 79 and a zirconium oxide film 81 are formed on the surface of the silicon wafer 78 one after another. A conductive film is formed on a surface of the zirconium oxide film 81. The conductive film is constructed as a layered film of titanium, iridium, platinum, and titanium. The lower electrode 24, the extraction wiring 27, and the lower electrode terminals 33, 35 are formed from the conductive film by a photolithographic technique.

Figure 8:
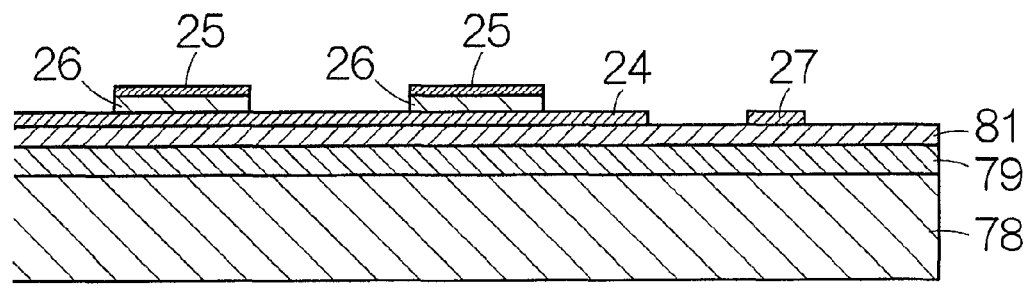
FIG. 8 is a partially enlarged vertical sectional view schematically showing a piezoelectric film and an upper electrode formed on the lower electrode.

As shown in FIG. 8, the piezoelectric film 26 and the upper electrode 25 are formed on a surface of the lower electrode 24 per each element 23. Prior to forming the piezoelectric film 26 and the upper electrode 25, a piezoelectric material film and a conductive film are formed on the surface of the silicon wafer 78. The piezoelectric material film is constructed of a PZT film. The conductive film is constructed of an iridium film. The piezoelectric film 26 and the upper electrode 25 are formed from the piezoelectric material film and the conductive film per each element 23 by a photolithographic technique.

Figure 9:
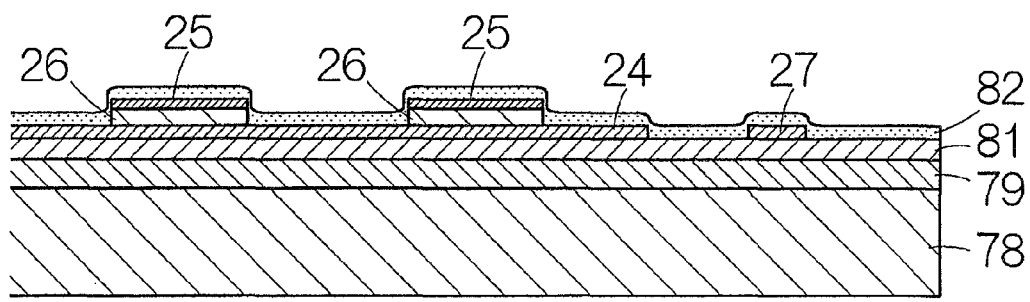
FIG. 9 is a partially enlarged vertical sectional view schematically showing a conductive film that covers the silicon wafer.

Next, as shown in FIG. 9, a conductive film 82 is formed on the surface of the silicon wafer 78. The conductive film 82 connects the upper electrodes 25 with respect to each other per column in each element chip 17. The upper electrode 25 and the upper electrode terminals 34, 36 are formed from the conductive film 82 by a photolithographic technique.

Figure 10:
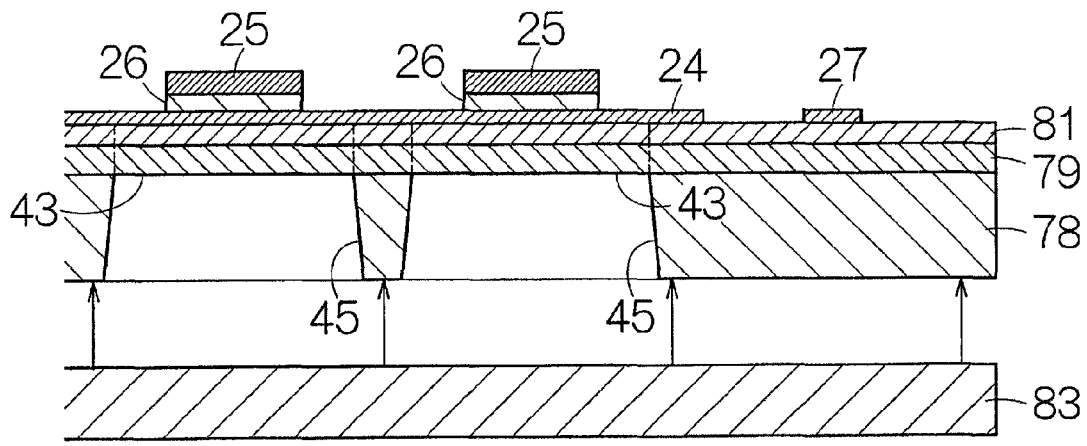
FIG. 10 is a partially enlarged vertical sectional view schematically showing an opening formed in the silicon wafer, and a wafer for a reinforcing plate.

Next, as shown in FIG. 10, the openings 45 of an array pattern are formed from the rear surface of the silicon wafer 78. For forming the openings 45, an etching treatment is conducted. The silicon oxide film 79 serves as an etching stop layer. The vibrating film 43 is divided into the silicon oxide film 79 and the zirconium oxide film 81. After the openings 45 are formed, a surface of a wafer 83 for a reinforcing plate is layered on the rear surface of the silicon wafer 78. For example, a rigid insulating substrate can be used for the wafer 83. A silicon wafer can be used for the insulating substrate. For example, an adhesive can be used for bonding. After bonding, each of the element chip 17 is cut out of the silicon wafer 78.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the ultrasonic diagnostic device 11, the ultrasonic probe 13, the element chip 17, the element 23 and the like are not limited to the present embodiment, and various changes and modifications are possible.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer element chip comprising:
a substrate including a partition wall section defining a plurality of openings arranged in an array pattern, a wall thickness of the partition wall section being smaller than a wall height of partition wall section;
a plurality of ultrasonic transducer elements with each of the ultrasonic transducer elements being provided in each of the openings; and
a plate-shaped member fixed on a surface of the substrate opposite to a surface of the substrate on which the ultrasonic transducer elements are provided, the plate-shaped member covering at least one of the openings in a plan view seen along a thickness direction of the substrate.

2. The ultrasonic transducer element chip according to claim 1, wherein
the plate-shaped member is bonded to at least one bonding region of the partition wall section.

3. The ultrasonic transducer element chip according to claim 1, wherein
the partition wall section is arranged so that an outline of each the openings is defined as a quadrangle.

4. The ultrasonic transducer element chip according to claim 3, wherein
the quadrangle has two opposed long sides, and the bonding region of the partition wall section is a region including a center position of each of the long sides.

5. The ultrasonic transducer element chip according to claim 4, wherein
the bonding region of the partition wall section is a region including an entire length of each of the long sides.

6. The ultrasonic transducer element chip according to claim 5, wherein
the partition wall section is surface-bonded to the plate-shaped member over an entire surface corresponding to each of the long sides disposed between the openings.

7. The ultrasonic transducer element chip according to claim 3, wherein
the partition wall section corresponding to each side of the quadrangle includes the bonding region.

8. The ultrasonic transducer element chip according to claim 7, wherein
the bonding region of the partition wall section continuously surrounds the quadrangle.

9. The ultrasonic transducer element chip according to claim 8, wherein
the partition wall section is surface-bonded to the plate-shaped member over an entire surface corresponding to an entire periphery of the quadrangle.

10. A probe comprising:
the ultrasonic transducer element chip according to claim 1; and
a case member supporting the ultrasonic transducer element chip.

11. An electronic instrument comprising:
the probe according to claim 10; and
a processing circuit connected to the probe and configured to process an output signal from the ultrasonic transducer element.

12. An ultrasonic diagnostic device comprising:
the probe according to claim 10;
a processing circuit connected to the probe and configured to process an output signal from the ultrasonic transducer element to generate an image; and
a display device configured to display the image.

13. A probe head comprising:
the ultrasonic transducer element chip according to claim 1; and
a case member supporting the ultrasonic transducer element chip, and configured to be coupled to a probe main body.

\* \* \* \* \*